(12) United States Patent
Mishra et al.

(10) Patent No.: US 8,496,964 B2
(45) Date of Patent: Jul. 30, 2013

(54) CONTROLLED RELEASE MICRO-CAPSULE FOR OSTEOGENIC ACTION

(75) Inventors: Prabhat Ranjan Mishra, Lucknow (IN); Ritu Trivedi, Lucknow (IN); Girish Kumar Gupta, Lucknow (IN); Avinash Kumar, Lucknow (IN); Varsha Gupta, Lucknow (IN); Srikanta Kumar Rath, Lucknow (IN); Kamini Srivastava, Lucknow (IN); Naibedya Chattopadhyay, Lucknow (IN); Anil Kumar Dwivedi, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/203,603

(22) PCT Filed: Feb. 26, 2010

(86) PCT No.: PCT/IN2010/000115
§ 371 (c)(1),
(2), (4) Date: Aug. 26, 2011

(87) PCT Pub. No.: WO2010/097814
PCT Pub. Date: Sep. 2, 2010

(65) Prior Publication Data
US 2011/0305754 A1   Dec. 15, 2011

(30) Foreign Application Priority Data

Feb. 27, 2009   (IN) .............................. 384/DEL/2009

(51) Int. Cl.
| | |
|---|---|
| *A61K 9/52* | (2006.01) |
| *A61K 9/50* | (2006.01) |
| *A61K 31/70* | (2006.01) |
| *B01J 13/00* | (2006.01) |
| *B05D 3/00* | (2006.01) |
| *A01N 43/04* | (2006.01) |

(52) U.S. Cl.
USPC ............................ 424/457; 427/2.21; 514/23

(58) Field of Classification Search
None
See application file for complete search history.

(56) References Cited

U.S. PATENT DOCUMENTS

| 2007/0116836 A1* | 5/2007 | Prakash et al. ................. 426/548 |
| 2007/0184098 A1* | 8/2007 | Moussou et al. ............... 424/450 |
| 2007/0207212 A1* | 9/2007 | Haynie et al. .................. 424/490 |
| 2007/0224345 A1* | 9/2007 | Metz et al. ..................... 427/212 |

FOREIGN PATENT DOCUMENTS

WO   WO 2008072155 A1 *  6/2008

OTHER PUBLICATIONS

Aerssens et al. (1998). "Interspecies differences in bone composition, density, and quality: potential implications for in vivo bone research". Endocrinology, 139(2): 663-670.*
D'Archivio et al. (2010). "Biovailability of the Polyphenols: Status and Controversies". International Journal of Molecular Sciences., 11: 1321-1342.*
PubMed Health. "Osteogenesis imperfecta"., http://www.ncbi.nlm.nih.gov/pubmedhealth/PMH0002540/, accessed on Nov. 2, 2012.*
PubMed Health. "Fibrous Dysplasia"., http://www.ncbi.nlm.nih.gov/pubmedhealth/PMH0002214/, accessed on Nov. 2, 2012.*
esa A Dionex Compony., "The Measurement of Resveratrol, Kaempferol,Quercetin and Isorhamnetin in Human Plasma". Application Note., p. 1-5, http://www.esainc.com/docs/spool/70-4997P_Resveratrol.pdf, accessed on Nov. 2, 2012).*
Oliveira et al (2000). "In vitro glucuronidation of kaempferol and quercetin by human UGT-1A9 microsomes". FEBS Letters, 471: 1-6.*

* cited by examiner

*Primary Examiner* — Robert T Crow
*Assistant Examiner* — Doan Phan
(74) *Attorney, Agent, or Firm* — Abelman, Frayne & Schwab (57) ABSTRACT

The present invention relates to a microcapsule for controlled release of flavanoid compound and a process for preparation thereof. The microcapsule comprising a core particle consisting of a calcium salt, Pluronic F68 [poly (ethylene oxide-co-polypropylene oxide), block poly oxyethylene-polypropylene block copolymer], loaded with a flavanoid compound, the resulting core particle having a plurality of alternate layers of cationic and anionic polyelectrolytes adsorbed thereon and an outer layer formed by a bile salt, wherein the flavanoid is ranging between 10 to 96% by weight.

13 Claims, 6 Drawing Sheets

CONTROLLED RELEASE MICRO-CAPSULE FOR OSTEOGENIC ACTION

RELATED APPLICATIONS

This application is a §371 of PCT/IN2010/000115 filed Feb. 26, 2010, and claims priority from Indian Patent Application No. 384/DEL/2009 filed Feb. 27, 2009, both incorporated by reference in their entirety.

FIELD OF THE INVENTION

The present invention relates to a micro-capsule for controlled release of flavanoid compound for osteogenic action. The present invention particularly relates to a micro-capsule for controlled release of flavanoid compound using the layer by layer technology. Kaempferol (K) has bone anabolic action.

BACKGROUND OF THE INVENTION

The mainstay of osteoporosis treatment remains anti-resorptive approach by way of bisphosphonates. Bisphosphonate treatment prevents further bone loss but is ineffective for making up lost bone. Bone forming (osteogenic/anabolic) therapy, which is the ultimate goal for osteoporosis treatment, is limited only to parathyroid hormone (PTH). In addition to being extremely costly, PTH is not readily available in India. Lately, reports of development of osteosarcoma as a result of prolonged use of PTH have been reported. Therefore, finding new bone anabolic agent, that is safe and could increase bone mass and strength and thereby reducing the risk of osteoporotic fracture is an unmet medical need.

Epidemiological as well as in vitro studies suggest that consumption of flavonoids is beneficial for bone health. Majority of the studies on the effects of flavonoids in bone involve isoflavones. Isoflavones such as genistein and diadzein are phytoestrogens with strong anti-osteoclastogenic actions. Isoflavone-rich soy food has been tested in clinical trials with mixed results (Horcajada et al 2000, Ma D F et al 2008). Kaempferol was reported as phytoestrogen and can be used as therapeutic agent for osteoblasts (PCT publication no. WO 2005/077358 A1 dated 25 Aug. 2005). A composition comprising gum Arabic with acacia derivatives has also been used for the conditions of osteoporosis, which has been reported to promote calcium absorption (PCT/EP 2008/006462). Comparative bioavailability of different flavonols has been reported after administration of three different preparations i.e capsules, drops and tablets of gingko biloba, of which, drops have shown higher absorption. Kaempferol (K) is structurally similar to quercetin and contributes about 25-33% of mean total flavonol intake in human, which estimates at 6-10 mg per day in the USA and the Netherlands.

Kaempferol is reported to have anti-oxidant, anti-viral, anti-bacterial, cardio-protecting (prevent atherosclerotic plaque formation) and chemo-preventive properties. It is a non-steroidal phytoestrogen that acts like hormone estrogen. More recently their activity in breast cancer and as anti-osteoporosis, mediated via estrogen receptor, is an active area of research.

It has been reported that gum Arabic and acacia derivatives has tendency to promote calcium absorption when given orally (PCT/EP 2008/006462). Gingko biloba extract after administration of three different preparations in the form of capsules, drops and tablets, it has been observed that drops have shown higher absopriton (Wojcicki J, Gawronska-Szklarz, B, Bieganowski, W Patalan, M, Smulski, H K, Samochowiec, L, Zakrzewski, J. Mater. Med. Pol. (1995) 27(4) 141-146. Kaempferol (K) is structurally similar to quercetin and contributes about 25-33% of mean total flavonol intake in human, which estimates at 6-10 mg per day in the USA and the Netherlands [Hertog M G, Hollman P C, Katan M B, Kromhout D., Nutr. Cancer. 1993, 20:21-29; Sampson L, Rimm E, Hollman P C, DeVries J H, Katan M B., J. Am. Diet Assoc. 2002, 102:1414-1420]. The use of biodegradable nano-matrix formulations by layer-by-layer (LbL) adsorption technique represents an alternative to other colloidal carriers viz: liposomes, niosomes, bilosomes, aquasomes, nanoparticles and microparticles as well as for delivering the large quantities of water soluble as well as water insoluble (hydrophilic/hydrophobic) drugs for controlled delivery and better targeting efficacy [Bentina, 1996; Allen and Cullis, 2004; Brigger et al., 2002; Totchilin, 2005 Bentina, S. (Ed.) 1996; Microencapsulation, Drugs and the Pharmaceutical Science. Marecl Dekker, New York; Allen, T. M., Cullis, P. R., 2004; Drug Delivery systems: entering the mainstream. Science 303, 1818-1822; Brigger, I., Dubernet, C., Couvreur, P., 2002; Nanoparticles in cancer therapy and diagnosis. Adv. Drug Deliv. Rev. 54, 631-651; Totchilin, V. P., 2005; Recent advances with liposome as pharmaceutical carriers, Nat. rev. Drug Discov. 4, 145-160]. Though all these mentioned techniques/technologies fulfill the optimal delivery of drugs with improved performance within the specified cell or tissue however, these technologies have come to an age and altogether transformed into mature discipline. The excipient used in the proposed systems are generally regarded as safe (GRAS) and is preferably approved by the USFDA.

Recently developed, porous microparticles (MP) of inorganic origin have a great potential to allocate the drug in their nanopores (nanoreservoir) and having features of biological stability with sustained release property. Most of researchers have reported use of porous architecture for fabrication of assembly viz. porous hollow silica nanoparticles [Li, Z. Z., Wen, L. X., Shao, L., Chen, J. F. Fabrication of porous hollow silica nanoparticles and their applications in controlled drug release. [J. Control Rel. 2004, 98, 245-254], porous hydroxyapatite [Kim, H. W., Knowles, J. C., Kim, H. E., Hydroxyapatite/poly (ε-caprolactone) composite coatings on hydroxyapatite porous bone scaffold for drug delivery. Biomaterials 2004, 25, 1279-1287], porous calcium carbonate microparticles [Volodkin, D. V., Larionova, N. I., Sukhorukov, G. B.,. Protein encapsulation via porous $CaCO_3$ microparticles templating. Biomacromolecules 2004, 5, 962-972; Volodkin, D. V., Petrov, A. I., Prevt, M., Sukhorukov, G. B., Matrix polyelectrolyte microcapsules: new system for macromolecule encapsulation. Langmuir 2004, 20, 3398-3406] and other porous architecture. The novel approach in this regard is the development of smart, functional, organized system by LBL self-assembling technique for the micro-encapsulation of bioactives [Caruso, F., Nano engineering of particle surface Adv. Mater. 2001, 13, 11-22; Peyratout, C. S., Dahne, L., Tailor-made polyelectrolyte microcapsules: from multilayers to smart containers. Angew. Chem. Int. ed. 2004, 434, 3762-3783; Decher, G., Schlenoff, J. B. (Eds.), 2003. Multilayer Thin films: Sequential Assembly of Nanocomposite Material. Wiley-VHC, Weinheim].

Among the decomposable core, porous $CaCO_3$ MP elicits interest due to its wide industrial, technological and drug delivery applications [Caruso F., Caruso R. A, Mohwald H., Nanoenginnering of inorganic and hybrid hollow spheres by colloidal templating, Science, 1998, 282, 1111-1114; Ye S., Wang C., Liu X., Tong Z., Deposition temperature effect on release rate of indomethacin microcrystals from microcapsules of layer-by-layer assembled chitosan and alginate multilayer films, J. Control. Release, 2005, 106, 319-328; Donath E., Moya S., Neu B., Sukhorukov G. B., Georgieva R., Voigt A., Baumler H., Kiesewetter H., Mohwald H., Hollow polymer shells from biological templates: fabrication and potential applications, Chem. Eur. J., 2002, 8, 5481-5485; An, Z. H., Lu G., Mohwald H., Li J. B., Self assembly of human serum albumin and L-alpha-dimyristoylphosphatidic acid (DMPA) microcapsules for controlled drug release, Chem. Eur. J., 2004, 10 5848-5852]. The powder XRD data reveals (illustrated in FIG. 1A) that all polymorphic forms of the $CaCO_3$ have been obtained during fabrication of porous particles viz: calcite (rhombohedral), aragonite (hexagonal) and vaterite (spherical) due to mutual transformation between them (Volodkin, D. V., Larionova, N. I., Sukhorukov, G. B., Protein encapsulation via porous $CaCO_3$ microparticles templating. Biomacromolecules 2004, 5, 962-972) using conventional method of co-precipitation of calcium chloride dihydrate and sodium carbonate. Lactalbumin was encapsulated by means of the proposed technique yielding a content of 0.6 pg protein per microcapsule. Horseradish peroxidase saves 37% of activity after encapsulation. However, the thermostability of the enzyme was improved by encapsulation. The results demonstrate that porous $CaCO_3$ microparticles can be applied as microtemplates for encapsulation of proteins into polyelectrolyte capsules at neutral pH as an optimal medium for a variety of bioactive material, which can also be encapsulated by the proposed method. Volodkin et al., 2004b proposed a new approach to fabricate polyelectrolyte microcapsules is based on exploiting porous inorganic microparticles of calcium carbonate. The structural investigations on multilayer composed of strong flexible PE's revealed that enzymes can be incorporated in multilayer for either biosensing or multistep biocatalysts. [Decher et al., Curr Opin Coll Interface Sci 3: 32-9 1998]. Volodkin et al., [Langmuir, 2: 3398-3406 (2004a)], used porous microparticles of calcium carbonate for encapsulation of protein in polymer-filled microcapsules by means of electrostatic layer-by-layer assembly. Porous inorganic microparticles of calcium carbonate has been proposed as new approach to fabricate polyelectrolyte microcapsules [Volodkin et al., Langmuir, 2: 3398-3406 2004b]. Caruso [Adv. Mater. 13, 11-22 2001]; reviewed the creation of core-shell particles and its application as building blocks for photonic crystals, in multi-enzyme biocatalysts, and in drug delivery. A novel encapsulation method for ibuprofen (IBU) on porous $CaCO_3$ MP doped with polystyrene sulfonate (PSS) by combination of methods using LbL assembly has been studied by [Wang et al., Journal of material chemistry, 2007]. Schlenoff et. al. 2001, studied the growth of multilayers made from a combination of a weak polyacid and a strongly dissociated polycation as a function of salt concentration and molecular weight. Gao et al., [Langmuir, 7: 3491-3495 (2001)] developed a drug delivery system based on spontaneous deposition of soluble, low molecular weight therapeutic agents for the purpose of sustaining drug release. LbL assembly of oppositively charged PE's onto melamine formaldehyde colloidal particles, followed by core removal at low pH has yielded intact hollow microcapsules. Gupta et al., 2008, has successfully allocated paclitaxel (PTX). in their nanopores (nanoreservoir) and reported biological stability along with sustained release properties. Bhadra et al., 2004, successfully carried out comparative study on development and characterization of the multicomposite architecture using calcium phosphate and RBC as core particles for LbL assembly. The elasticity of the capsules can be made to vary within 0.05-10 GPa, depending on the composition, treatment and filling of the capsule [Fery and Vinogradova, New J. Phys. 6, 1-13, 2004]. Studies from our laboratory have revealed that Kaempferol exerts bone sparing action in OVx rats by stimulating bone formation. Kaempferol treatment to OVx rats resulted in the increase in osteoprogenitor cells as well as inhibition of adipocyte differentiation from bone marrow cells compared with the OVx group treated with vehicle. In addition, Kaempferol has no estrogen agonistic effect at the uterine level. Thus, Kaempferol has therapeutic promise for postmenopausal bone loss. However, one of the major challenges in developing Kaempferol as therapeutics for osteoporosis is their rapid elimination from the body after oral administration and poor oral bioavailability (Scalbert et al, Crit. Rev Food Sci. Nutr. 45(4) 287-306 (2005)]; Trivedi et al, Mol. Cell. Endo. 289; 85-93 (2008)]. It has been observed that Kaempferol undergo post-absorption sharp elimination phase which eventually go below detection limit after 6 hr. However, there exists a distinct scope for improvement in the case of Kaempferol for therapeutic use, by increasing its bioavailability. Better bioavailability would enhance anti-osteoporotic effects of Kaempferol as well as reduce its dose (indicating better safety).

OBJECTS OF THE PRESENT INVENTION

The main object of this invention is to provide a controlled release micro-capsule for improved osteogenic action.

Another object of the present invention is to provide the pharmaceutically acceptable Kaempferol preparation with a high drug payload.

Further objective of the present invention is to deliver Kaempferol in the form of a nano matrix.

Yet another object of the present invention is to provide a pharmaceutically acceptable Kaempferol preparation without potentially toxic organic solvents.

Yet another object of the present invention is to provide a formulation of Kaempferol, which can sustain the drug release for prolonged time in serum and bone marrow.

Further object of the present invention is to provide stable formulation, which can be used for the treatment of osteoporosis.

Yet another object of the present invention is to provide stable formulation, which can be used for early repair of bone fracture.

DEFINITIONS

Bioavailability: Bioavailability is a measurement of the rate and extent of a therapeutically active drug that reaches the systemic circulation and is available at the site of action.

GRAS: Generally Regarded As Safe.

Layer-by-Layer:

A microencapsulation of a layer on another layer, having opposite charge on a biodegradable core using biocompatible and biodegradable polyelectrolytes.

SUMMARY OF THE INVENTION

Accordingly the present invention provides a micro-capsule for controlled release of flavanoid compound comprising a core particle consisting of a calcium salt, PLURONIC F-68 [poly (ethylene oxide-co-polypropylene oxide) block poly oxyethylene-polypropylene block copolymer], loaded with a flavanoid compound, the resulting core particle having a plurality of alternate layers of cationic and anionic polyelectrolytes adsorbed thereon and an outer layer formed by a bile salt, wherein the flavanoid is ranging between 10 to 96% by weight.

In an embodiment of the invention, the flavanoid compound is selected from the group consisting of kaempferol and its derivatives, quercetin, and its derivatives, rutin, C-glycosylated and O-glycosylated kaempferol.

In another embodiment of the present invention, the polyelectrolyte is selected from a group consisting of naturally occurring polymers including sodium alginate, protamine sulfate chitosan, glycol chitosan and alginate, similarly synthetic polymers including poly allylamine hydrochloride, poly styrene sulfonate, polyornithine bromide, poly lysine, poly ethylene imine and a combination thereof.

In a further embodiment of the invention, the polyelectrolytes comprising both cationic and anionic PE's. (the polyelectrolytes.

In yet another embodiment of the present invention, the polyelectrolyte is biocompatible and biodegradable.

In an embodiment of the invention, the polyelectrolyte comprises weak positively charged polyelectrolytes selected from the group consisting of protamine sulfate, chitosan, glycol chitosan and weak negatively charged polyelectrlolytes selected from the group consisting of sodium alginate, dextran sulphate fluorescene isothiocyanate dextran sulfate (FITC-DEX).

In yet another embodiment of the present invention, the naturally occurring polyelectrolytes is selected from a group consisting sodium alginate, protamine sulfate chitosan, glycol chitosan and alginate.

In yet another embodiment of the present invention, the core particle is selected from the group consisting of β-tricalcium phosphate, hydroxyapatite, calcium carbonate, calcium sulphate, calcium phosphate, bone and demineralized bone.

In an embodiment of the invention the bile salts are selected from the group consisting of Sodium cholate, Sodium taurocholate, Sodium glycocholate, Sodium deoxycholate (SDC), Sodium taurodeoxycholate (STDC), Sodium glycodeoxycholate, Sodium ursodeoxycholate, Sodium chenodeoxycholate, Sodium taurochenodeoxycholate, Sodiumglyco chenodeoxycholate, Sodium cholylsarcosinate, Sodium N-methyl taurocholate.

In another embodiment of the present invention, the bioavailability of flavonoid in serum is 166% higher as compared to free kaempferol and in bone marrow the bioavailability has been enhanced by 300% as compared to free kaempferol.

In yet another embodiment of the present invention, the cumulative % flavanoid release from fabricated micro-capsules is 19.2% and 63.5% in simulated gastric fluid (SGF) and simulated intestinal fluid (SIF) respectively after 24 h.

In yet another embodiment of the present invention, the micro-capsule enhances bone mineral density by 8 to 20%.

In another embodiment of the present invention, the microcapsule enhances bone strength by 20 to 25%.

In another embodiment of the present invention, the microcapsule is based on layer-by-layer technology, which involves electrostatic interaction between polyelectrolytes to get a nanomatrix to control the release of active ingredient.

In still another embodiment of the present invention, the microcapsule is useful for the treatment of osteoporosis, bone healing in case of bone fracture and assist bone regeneration during fracture healing, increase bone formation and bone mineral density during growth and optimize peak bone mass or to decrease bone loss, in particular bone loss associated with age in humans or pets. In an embodiment of the present invention, a process for preparation of a micro-capsule for controlled release of flavanoid. The process steps comprises:

(a) mixing equimolar concentration of calcium chloride dehydrate and sodium carbonate in presence of PLU-RONIC F-68 to obtain porous, spherical and homogeneously dispersed particles of $CaCO_3$ micro particles, (b) incubating $CaCO_3$ micro particles with flavanoid in monohydric alcohol as a solvent for a period ranging between 12 to 36 h and finally washing thoroughly and drying under vacuum at a temperature ranging between 30 to 50 degree C., (c) depositing alternatively, the oppositely charged weak PE's on flavanoid loaded $CaCO_3$-Kaempferol using layer-by-layer assembly to obtain polyelectrolyte (PE) nanomatrix, (d) incubating the said polyelectrolyte (PE) nanomatrix with a solution of bile salt for surface modification at a temperature ranging between 20 to 40 degree centigrade for a period ranging between 30 minutes to two hr, centrifuging followed by washing with water to obtain the micro-capsule.

In an embodiment of the present invention, the microcapsule given orally, the auto-digestion of core particles in GI milieu and thus transformation of these micro-capsules in to nano-walled matrix facilitates penetration of flavanoid in to lymphatic route through peyer's patches and lacteals and thus showing enhanced levels of flavanoid in serum and bone marrow.

In an embodiment of the present invention, orally inducing osteogenic effect into mammalian bone tissue in a patient in need of such treatment comprising administration of the microcapsule consisting essentially of flavanoid in an amount effective to induce synergistic osteogenic effect of flavanoids using pharmaceutically acceptable and pharmacologically inactive excipients.

In another embodiment of the present invention, use in controlled release composition and simultaneously enhancing circulating half-life improving specificity and absorption in bone marrow wherein the method comprises: administering the microcapsule to the subject in need for the treatment.

In yet another embodiment of the present invention, the micro-capsule is used in the treatment and/or prophylaxis of age related osteoporosis in pets and humans, alleviation or prevention of bone disorder or maintenance of bone health, the method comprises administering a therapeutically-effective amount of the micro-capsule to an individual in need of such treatment.

DETAILED DESCRIPTION OF THE INVENTION

The present invention relates to drug delivery system comprising at least one pharmaceutically active agent, at least two polyelectrolytes (biocompatible and biodegradable) of different charge, one bile salt, excipients for preparation of porous core particles and a nonionic surfactant during preparation of core particles to maintain the sphericity and stability of inorganic core particles. A particular advantage of the present invention is that it provides a simple and inexpensive system to facilitate the administration of medicaments. In many embodiments, this drug delivery system enhances the stability and bioavailability of pharmaceutically active agents, synergistically effective for desired pharmacological action.

Pharmaceutical formulations may be administered through various routes of administration. For example, formulations may be administered orally and intravenously. The encapsulation of pharmaceuticals as biodegradable microcapsule is useful in reducing toxicity and improving the therapeutic effectiveness of Kaempferol. Further, this can be applied to certain other drugs for example, gingko biloba, quercetin, rutin, flavonoids, isoflavonoids after encapsulation into nanomatrix.

In vitro, Kaempferol has various functions in bone cells including inhibition of osteoclast differentiation from their precursor cells, induction of osteoclast apoptosis and inhibition of osteoclastogenic cytokine production from osteoblasts. Studies from our laboratory have revealed that Kaempferol exerts bone sparing action in OVx rats by stimulating bone formation. Kaempferol treatment to OVx rats resulted in the increase in osteoprogenitor cells as well as inhibition of adipocyte differentiation from bone marrow cells compared with the OVx group treated with vehicle. In addition, Kaempferol has no estrogen agonistic effect at the uterine level. Thus, Kaempferol has therapeutic promise for postmenopausal bone loss. However, one of the major challenges in developing Kaempferol as therapeutics for osteoporosis is their rapid elimination from the body after oral administration and poor oral bioavailability (Scalbert et al, 2005; Trivedi et al, 2008). It has been observed that Kaempferol undergo post-absorption sharp elimination phase which eventually go below detection limit after 6 hr. However, there exists a distinct scope for improvement in the case of Kaempferol for therapeutic use, by increasing its bioavailability. Better bioavailability would enhance anti-osteoporotic effects of Kaempferol as well as reduce its dose (indicating better safety).

We have developed Kaempferol as a sustained release formulation which will be in the form of nanomatrix with a blend of biocompatible and biodegradable polyelectrolytes (PE's), and then studied its potentially positive impact on skeletal health in vivo. This developed formulation has been evolved as suitable delivery systems for stability as well as sustaining property of Kaempferol which may be of commercial interest for effective management of osteoporosis.

Weak Polyelectrolyte (PE's):

The use of weak PE's rather than small molecules is advantageous mainly because of good adhesion of a layer to the underlying substrate or films require certain number of ionic bonds. Therefore, the overcompensation of the surface charge by the incoming layer is more a property of the polymer than a property of the surface. This is because polymer can simply bridge over underlying defects; their conformation at the surface (and thus newly created film surface) is mostly dependent on the chosen PE's and adsorption condition and much less dependent on the substrate or the substrates charge density.

| List of polyelectrolyte | |
|---|---|
| Compound | Commercial product (Supplier) |
| Polycations | |
| Poly (allyamine hydrochloride), PAH | (Sigma aldrich), (USA), |
| Protamine sulfate, PRM | (Sigma aldrich), (USA), |
| Poly(dimethyldiallyl ammonium chloride), PDDA | (Sigma aldrich), (USA), |
| Polyethyleneinme (PEI) | (Sigma aldrich), (USA), |
| Chitosan | (Sigma aldrich), (USA), |
| Glycol chitosan, GC | (Sigma aldrich), (USA), |
| Polyanions | |
| Poly (styrenesulfonate sod.), PSS | (Sigma aldrich), (USA), |
| Sodium alginate, SA | (Sigma aldrich), (USA), |
| Dextran Sulfate, DEX | (Sigma aldrich), (USA), |
| Fluorescene isothiocynate dextran Sulfate (FITC-DEX) | (Sigma aldrich), (USA), |

In an embodiment, the simple and modified co-precipitation method includes preparation of an inorganic core particle by addition of nonionic surfactant, which provides stable, porous, monodisperse and spherical core particles. In one aspect the porosity of the core particles has been used for the allocation of drug molecules in their nano-pores using the polarity gradient of the organic solvent in which drug has to be solubilized.

Organic Solvent for Entrapment of Kaempferol:

Methanol is suitable organic solvent for use in the present invention. Among those organic solvents (Hexane, Acetonitrile, Dimethylformamide, Dimethyl sulphoxide, Ethanol), preferred one is monohydric alcohol because of nontoxic nature and high polarity to penetrate the Kaempferol into the nanopores of $CaCO_3$ MP. Examples of these organic solvents are shown below with their polarity.

| Solvent | Polarity ($\epsilon$ at 25° C.) |
|---|---|
| Dimethylsulfoxide | 46.7 |
| Dimethylformamide | 37.8 |
| Dimethylacetamide | 37.8 |
| Ethanol | 24.5 |
| Hexane | 1.88 |

Figure 1:
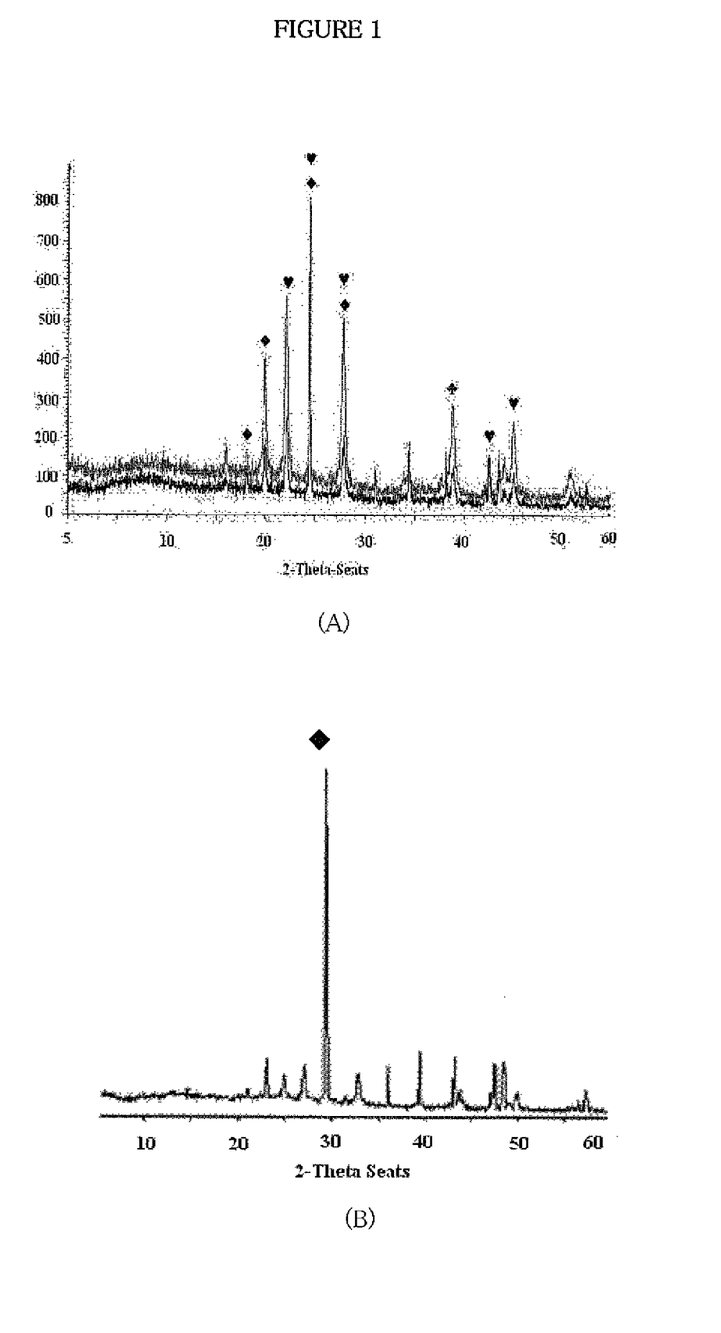
FIG. 1: XRD pattern of different polymorphs of porous $CaCO_3$ core microparticles. A: Core particle prepared by conventional method (co-precipitation of calcium chloride dihydrate and sodium carbonate; B: Core particle prepared by modified method (co precipitation in presence of PLURONIC F-68). ♣ Aragonite (Hexagonal), ♥ Calcite (Rhombohedral), ■ Vaterite (Spherical).

The powder XRD data reveals (illustrated in FIG. 1A) that all polymorphic forms of the $CaCO_3$ have been obtained during fabrication of porous particles viz: calcite (rhombohedral), aragonite (hexagonal) and vaterite (spherical) due to mutual transformation between them (Volodkin, D. V., Larionova, N. I., Sukhorukov, G. B., Protein encapsulation via porous $CaCO_3$ microparticles templating. Biomacromolecules 2004, 5, 962-972) using conventional method of co-precipitation of calcium chloride dihydrate and sodium carbonate. However, to our interest vaterite polymorph having uniform and spherical morphology was desirable as it is anticipated to provide uniform and amplified surface area so as to obtain uniform coating of PEs and high payload of bioactives. Modification of conventional procedure by incorporating appropriate concentration of PF-68 during controlled co-precipitation lead to the formation of vaterite polymorph in abundance as shown in FIG. 1B. These polymorph were perfectly spherical, non-aggregated and monodisperse in the size range of 3-5 μm as demonstrated by scanning electron microscopy (SEM, as illustrated in FIG. 2A). The controlled crystallization of $CaCO_3$ resulting in the formation of uniform, homogenous and non-aggregated MP. This effect could be ascribed to adsorption of PF-68 on the surface and thus preventing aggregation and crystallization. It has also been observed that the shape and morphology of $CaCO_3$ MP were remained unaltered during a storage period of at least three months. In one aspect of the invention, the method of preparing biodegradable microcapsules by encapsulating Kaempferol loaded core particles by PE's using LbL adsorption technique followed by surface modification with bile salts. In further embodiment of the invention, the pharmaceutically active agent is very poorly water-soluble drug.

Further the surface of the developed systems was modified with biologically oriented surface modification (bile salts) to facilitate cellular mediated endocytosis; and to control the specificity of interaction between the capsules and their target, to avoid difficulties with most of the drug delivery systems known in the prior art. For example, the utility of previous systems for orally administered labile pharmacological substances has been limited by the need to use toxic amounts of delivery agents, the instability of the systems, the inability to protect the active ingredient, the inability to effectively deliver drugs that are poorly water soluble or labile, the inadequate shelf life of the systems, the failure of the drug delivery systems to promote absorption of the active agent and the difficulties inherent to manufacturing the systems.

Among the various routes of drug administration, the oral route is preferred because of its ease of administration, safety and patient compliance. However, the therapeutic efficacy of many drugs (iso-flavones) in case of oral administration is reduced because of limited absorption through intestinal membrane, short half-life and short duration of action as well. The limited intestinal absorption and thus bioavailability may be due to extensive metabolism and/or efflux of the molecule (P-gp substrate) into GI lumen. Moreover, inorganic core particles, i.e. $CaCO_3$ are removed biologically at acidic environment in the stomach, and subsequently Kaempferol bearing nanomatrix is available for absorption from intestinal villi. With improved Kaempferol absorption the presence of $CaCO_3$ as integral core provided synergistic effect especially for the treatment of osteoporosis. Additionally employing bile salt as component of the formulation increases the absorption of the drug. Bile acids are naturally occurring surfactants. They are a group of compounds with a common 'backbone' structure based on cholanic acid found in all mammals and higher vertebrates. The detergent properties of bile acids are largely determined by the number and orientation of hydroxyl groups substituted onto a steroidal nucleus. Bile acids may be mono-, di- or tri-hydroxylated; they always contain a 3-alpha hydroxyl group, whereas the other hydroxyl groups, most commonly found at $C_6$, $C_7$ or $C_{12}$, may be positioned above (beta.) or below (alpha.) the plane of the molecule.

In another aspect of invention, our study has evidenced to have reduced one step in the preparation of nanomatrix. In the present invention, the core $CaCO_3$ particles automatically gets removed in the gastric fluid of stomach (in-vivo) after oral administration leaving behind the kaemferol loaded nanowalled matrix. This autogeneration of nanowalled matrix further facilitates its absorption in the GI tract as demonstrated in FIG. 4. That means, there is no need for prior removal of core particle before its administration.

In another aspect of the invention, a pharmaceutical formulation can be delivered in suspension and/or liquid suspension form.

Although the use of LbL assembly are independently known in the art, the delivery of Kaempferol along with $CaCO_3$ MP using bile salt as a integral shell component in the developed formulation has not been reported till date. Surprisingly, when bile salt is incorporated as an outer surface of the formulation, therapeutic efficacy of the drug is enhanced. In many embodiments of the present invent, this novel and unexpected enhancement, which results from the unique combination of $CaCO_3$ MP and Kaempferol along with bile salts in the formulation, relates to increased drug absorption and bioavailability as bile salt helps in enhanced absorption at specific site by providing long circulation half-life, by controlled delivery, by lymphatic absorption and finally due to its enterohepatic circulation and receptor mediated absorption present in the small intestine.

Bile Salts for Surface Modification

Bile salts used in formulations as said in this invention is the novelty to provide better absorption through intestinal villi. The bile salts over the charged surface have been adsorbed by simple electrostatic interaction between charge moieties. Examples of such bile salts are shown below.

| BILE SALTS | HLB value >10 |
|---|---|
| Sodium cholate | |
| Sodium taurocholate | |
| Sodium glycocholate | |
| Sodium deoxycholate (SDC) | |
| Sodium taurodeoxycholate (STDC) | |
| Sodium glycodeoxycholate | |
| Sodium ursodeoxycholate | |
| Sodium chenodeoxycholate | |
| Sodium taurochenodeoxycholate | |
| Sodium glyco chenodeoxycholate | |
| Sodium cholylsarcosinate and | |
| Sodium N-methyl taurocholate | |

In many embodiments of the current invention, the combination of a biofriendly inorganic core along with drug encapsulated into polymeric nanomatrix of natural origin overcomes the disadvantages of many existing novel drug delivery systems. In another aspect, it can be administered as suspension dosage form where it contains one but not more than two nonionic surfactant, one bile salt and one active medicament along with inorganic core, which helps as supportive therapy for osteoporosis along with Kaempferol.

Another aspect of the invention relates to a method for making drug delivery system comprising drug loaded core particles encapsulated by two biocompatible and biodegradable oppositely charged PE's followed by surface modification with SDC. Placebo may also be delivered according to certain embodiments of the invention.

Another aspect of the invention relates to state-of-art pilot study to determine probable absorption mechanism through intestinal wall using FITC-labeled formulation on living animal model. This work demonstrates that the surface chemistry of oral formulations can ultimately determine the fate and can aid in designing delivery vehicles for a variety of therapeutics currently plagued with poor oral bioavailability.

The delivery of the proposed systems to cells and organs although the outer surfaces of the capsules can be designed to be cell-specific, there is a need for biologically oriented surface modifications of the capsules to control the specificity of interaction between the capsules and their target. Polyelectrolyte multilayer capsules have been designed as potential drug carrier systems, where the capsule walls are made of biocompatible and biodegradable PE's (alginate, chitosan and other polysaccharides). Modifying the surface of the carriers with hydrophilic polymers such as poly (ethylene glycol) (PEG) has proven to be a successful strategy in making drug carriers resistant to protein adsorption, reducing unspecific cellular uptake and engineering long-circulating, inert, loaded capsules. Capsules coated with biologically inert PEG have already been fabricated, and capsules coated with biotin are highly effective in adhering to streptavidin surfaces. The delivery is provided by either specific (receptor-mediated) adhesion or guided by an external magnetic field. Following targeted delivery of the capsule, the uptake mechanism starts. At present, little experimental data are available concerning the interaction of PE capsules with biological cells. One important consideration in the passage of capsules through blood vessels is the capsule elasticity. As shown in the atomic-force spectroscopy studies performed by the groups of Fery and Vinogradova, the elasticity of the capsules can be made to vary to within 0.05-10 GPa, depending on the composition, treatment and filling of the capsule. This feature facilitates their use as a delivery system in the circulation. However, no animal data are available using this delivery system. It appears that, instead of their first introduction in 1998 by Decher, et al., capsule technology has not yielded any real applications, particularly data concerning capsule behavior in the bloodstream.

Surprisingly, the present invention have found that compositions including a combination of an inorganic core particles containing nonionic surfactant used for allocation of therapeutically effective amounts of hydrophobic therapeutic agents K, biocompatible and biodegradable PE's for encapsulation of drug loaded core particles, followed by surface modification with bile salts, thereby devoid the hydrophobicity and other disadvantages of conventional formulations. Use of these formulations results in an enhanced rate and/or extent of absorption of the Kaempferol and it can be extrapolated to other poorly soluble and short half-life drugs which have poor absorption profile. In one of our invention, it provides combination of different PE's of polycationic or polyanionic in nature for the LbL assembling over solid substrate either of inorganic origin or synthetic one.

Despite several reports on Kaempferol absorption and bioavailability there is no complete and perfect formulation of Kaempferol in terms of bioavailability and safety aspect in the market. In our laboratory an effort has been made towards the development of novel formulation using LbL adsorption technique to achieve better therapeutic efficacy of Kaempferol. To the best of authors' knowledge this is the first report comprising unique combination of components by layer-by-layer technology to deliver kaempferol showing enhanced bioavailability in the blood as well as in the bone marrow which is responsible for improved osteogenic activity.

The following examples broadly illustrate the nature of this invention the manner in which it is to be performed without limiting the nature and scope of the invention.

A: Synthesis of Porous and Spherical $CaCO_3$ Microparticles

Example-1

Porous and spherical $CaCO_3$ microparticles (MP) with a size 3.5 µm was prepared by colloidal crystallization from supersaturated (relative to $CaCO_3$) solution as reported by Volodkin et al. 2004 [Volodkin, D. V., Larionova, N. I., Sukhorukov, G. B.,. Protein encapsulation via porous $CaCO_3$ microparticles templating. Biomacromolecules 2004, 5, 962-972] with slight modification. Briefly, Ten ml volume of equimolar solution (0.33M) of calcium chloride dihydrate was added to equal volume of sodium carbonate containing 0.1% w/v of pluronic F-68 and thoroughly stirred for one minute. The MP thus obtained was thoroughly washed with Triple Distilled Water (TDW) followed by acetone and vacuum dried at temperature 50° C.

Example-2

Porous and spherical $CaCO_3$ microparticles (MP) with a size 3.5 µm was prepared by colloidal crystallization from supersaturated (relative to $CaCO_3$) solution as reported by Volodkin et al. 2004 [Volodkin, D. V., Larionova, N. I., Sukhorukov, G. B. Protein encapsulation via porous $CaCO_3$ microparticles templating. Biomacromolecules 2004, 5, 962-972] with slight modification. Briefly, Ten ml volume of equimolar solution (0.33M) of calcium chloride dihydrate was added to equal volume of sodium carbonate containing 0.2% w/v of pluronic F-68 and thoroughly stirred for one minute. The MP thus obtained was thoroughly washed with Triple Distilled Water (TDW) followed by acetone and vacuum dried at temperature 50° C.

Example-3

Porous and spherical $CaCO_3$ microparticles (MP) with a size 3.5 µm was prepared by colloidal crystallization from supersaturated (relative to $CaCO_3$) solution as reported by Volodkin et al. 2004 [Volodkin, D. V., Larionova, N. I., Sukhorukov, G. B. Protein encapsulation via porous $CaCO_3$ microparticles templating. Biomacromolecules 2004, 5, 962-972] with slight modification. Briefly, Ten ml volume of equimolar solution (0.33M) of calcium chloride dihydrate was added to equal volume of sodium carbonate containing 0.3% w/v of pluronic F-68 and thoroughly stirred for three minute. The MP thus obtained was thoroughly washed with Triple Distilled Water (TDW) followed by acetone and vacuum dried at temperature 30° C.

Example-4

Porous and spherical $CaCO_3$ microparticles (MP) with a size 3.5 µm was prepared by colloidal crystallization from supersaturated (relative to $CaCO_3$) solution as reported by Volodkin et al. 2004 [Volodkin, D. V., Larionova, N. I., Sukhorukov, G. B. Protein encapsulation via porous $CaCO_3$ microparticles templating. Biomacromolecules 2004, 5, 962-972] with slight modification. Briefly, Ten ml volume of equimolar solution (0.33M) of calcium chloride dihydrate was added to equal volume of sodium carbonate containing 0.4% w/v of pluronic F-68 and thoroughly stirred for one minute. The MP thus obtained was thoroughly washed with Triple Distilled Water (TDW) followed by acetone and vacuum dried at temperature 50° C.

B: Preparation of Drug Loaded Core Particles

Example-5

Dried $CaCO_3$ MP weighing 90 mg was incubated in drug (Kaempferol, 10% to 100% w/w concentration Kaempferol) solution using methanol as a solvent for 12 h in a closed batch to prevent evaporation of the solvent. Afterward, the suspension was brought into equilibrium under gentle stirring for 24 h. The Kaempferol-loaded $CaCO_3$ MP ($CaCO_3$-Kaempferol) were collected by centrifugation, washed with methanol to remove the adsorbed Kaempferol on the external surface, and dried in a vacuum oven at 50° C. temperature to completely evaporate the solvents from the impregnated materials. At the same time supernatant collected were analyzed for the determination of free drug using validated RP-HPLC developed in our laboratory. The amount of incorporated Kaempferol expressed as milligram Kaempferol/g $CaCO_3$ was evaluated by the difference of drug concentration in supernatant with the total amount taken for the incubation.

TABLE

Optimization of core to kaempferol ratio based on percent incorporation of kaempferol.

| S.No. | Amount of core CaCO3 taken (mg) | Amount of Kaempferol taken (mg) | Amount of Kaempferol loaded (mg) | % fraction of kaempferol loaded |
|---|---|---|---|---|
| 1 | 10 | 90 | 9.0 ± 1.17 | 10.4 ± 1.3% |
| 2 | 20 | 80 | 10.24 ± 1.36 | 12.8 ± 1.7% |
| 3 | 30 | 70 | 16.31 ± 12.73 | 23.3 ± 3.9% |
| 4 | 40 | 60 | 16.86 ± 1.56 | 28.1 ± 2.6% |
| 5 | 50 | 50 | 30.15 ± 2.1 | 60.3 ± 4.2% |
| 6 | 60 | 40 | 28.96 ± 2.24 | 72.4 ± 5.6% |
| 7 | 70 | 30 | 23.56 ± 1.02 | 78.6 ± 3.4% |
| 8 | 80 | 20 | 16.55 ± 0.62 | 82.9 ± 3.1% |
| 9 | 90 | 10 | 9.6 ± 0.24 | 96.1 ± 2.4% |

C: Fabrication of Microcapsules by Sequential Polyelectrolytes (PE's) Multilayer Example-6

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.1% w/v aqueous SA solution containing 0.5M NaCl into 0.5% w/v of the Kaempferol-loaded $CaCO_3$ MP. The mixture was incubated for 10 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.1% w/v aqueous PRM solution with 0.5M NaCl. This alternating SA and PRM layers were deposited in the identical way until the desired layer number was achieved and finally surface modification by using 0.1% w/v SDC solution containing in 0.5M NaCl by simple adsorption method. These Kaemperol loaded microcapsules were collected by centrifugation, rinsed with tripled distilled water. The concentration of microcapsules was determined by haemocytometer using following formula and was found to be 2×10⁷ Capsules/ml. Total number of capsules per cubic mm=

$$\frac{\text{Total No. of capsules} \times \text{Dilution} \times 4000}{\text{Total No. of square counted}}$$

$$\% \text{ Yield} = \frac{\text{Total No. of capsules per cubic mm}}{\text{Total No. of core particles per cubic mm}} \times 100$$

Example-7

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.1% w/v aqueous SA solution containing 0.5M NaCl into 1.0% w/v of the Kaempferol-loaded $CaCO_3$ MP. The mixture was incubated for 15 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.1% w/v aqueous PRM solution with 0.5M NaCl. This alternating SA and PRM layers were deposited in the identical way until the desired layer number was achieved and finally surface modification by using 0.1% w/v SDC solution containing in 0.5M NaCl by simple adsorption method. These Kaemperol loaded microcapsules were collected by centrifugation, rinsed with tripled distilled water. The concentration of microcapsules was determined by haemocytometer using formula as described in example 6 and was found to be ~2×10⁷ Capsules/ml.

Example-8

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.1% w/v aqueous SA solution containing 0.5M NaCl into 2.0% w/v of the Kaempferol-loaded $CaCO_3$ MP. The mixture was incubated for 10 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.1% w/v aqueous PRM solution with 0.5M NaCl. This alternating SA and PRM layers were deposited in the identical way until the desired layer number was achieved and finally surface modification by using 0.1% w/v SDC solution containing in 0.5M NaCl by simple adsorption method. These Kaemperol loaded microcapsules were collected by centrifugation, rinsed with tripled distilled water. The concentration of microcapsules was determined by haemocytometer using formula as described in example 6 and was found to be ~2×10⁷ Capsules/ml.

Example-9

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.1% w/v aqueous SA solution containing 0.5M NaCl into 3.0% w/v of the Kaempferol-loaded $CaCO_3$ MP. The mixture was incubated for 15 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.1% w/v aqueous PRM solution with 0.5M NaCl. This alternating SA and PRM layers were deposited in the identical way until the desired layer number was achieved and finally surface modification by using 0.1% w/v SDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be $\sim 2 \times 10^7$ Capsules/ml.

Example-10

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.2% w/v aqueous SA solution containing 0.5M NaCl into 0.5% w/v of the Kaempferol-loaded $CaCO_3$ MP. The mixture was incubated for 10 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.2% w/v aqueous PRM solution with 0.5M NaCl. This alternating SA and PRM layers were deposited in the identical way until the desired layer number was achieved and finally surface modification by using 0.2% w/v SDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be $\sim 2 \times 10^7$ Capsules/ml.

Example-11

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.2% w/v aqueous SA solution containing 0.5M NaCl into 1.0% w/v of the Kaempferol-loaded $CaCO_3$ MP. The mixture was incubated for 10 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.2% w/v aqueous PRM solution with 0.5M NaCl. This alternating SA and PRM layers were deposited in the identical way until the desired layer number was achieved and finally surface modification by using 0.2% w/v SDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be $\sim 2 \times 10^7$ Capsules/ml.

Example-12

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.2% w/v aqueous SA solution containing 0.5M NaCl into 2.0% w/v of the Kaempferol-loaded $CaCO_3$ MP. The mixture was incubated for 10 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.2% w/v aqueous PRM solution with 0.5M NaCl. This alternating SA and PRM layers were deposited in the identical way until the desired layer number was achieved and finally surface modification by using 0.2% w/v SDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be $\sim 2 \times 10^7$ Capsules/ml.

Example-13

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.2% w/v aqueous SA solution containing 0.5M NaCl into 3.0% w/v of the Kaempferol-loaded $CaCO_3$ MP. The mixture was incubated for 20 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.2% w/v aqueous PRM solution with 0.5M NaCl. This alternating SA and PRM layers were deposited in the identical way until the desired layer number was achieved and finally surface modification by using 0.2% w/v SDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be $\sim 2 \times 10^7$ Capsules/ml.

Example-14

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.1% w/v aqueous SA solution containing 0.5M NaCl into 0.5% w/v of the Kaempferol-loaded $CaCO_3$ MP. The mixture was incubated for 20 minute under gentle shaking. The excess PE's was removed by three repeated refine circles of centrifugation (4000 rpm, 4 min)/washing/re-dispersion in tripled distilled water. Subsequently the PRM layer was deposited sited using the same procedure with 10 ml 0.1% w/v aqueous PRM solution with 0.5M NaCl. This alternating SA and PRM layers were deposited in the identical way until the desired layer number was achieved and finally surface modification by using 0.1% w/v STDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be $\sim 2 \times 10^7$ Capsules/ml.

Example-15

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.1% w/v aqueous SA solution containing 0.5M NaCl into 1.0% w/v of the Kaempferol-loaded $CaCO_3$ MP. The mixture was incubated for 15 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.1% w/v aqueous PRM solution with 0.5M NaCl. This alternating SA and PRM layers were deposited in the identical way until the desired layer number was achieved and finally surface modification by using 0.1% w/v STDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be ~$2\times10^7$ Capsules/ml.

Example-16

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.1% w/v aqueous SA solution containing 0.5M NaCl into 2.0% w/v of the Kaempferol-loaded $CaCO_3$ MP. The mixture was incubated for 10 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.1% w/v aqueous PRM solution with 0.5M NaCl. This alternating SA and PRM layers were deposited in the identical way until the desired layer number was achieved and finally surface modification by using 0.1% w/v STDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be ~$2\times10^7$ Capsules/ml.

Example-17

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.1% w/v aqueous SA solution containing 0.5M NaCl into 3.0% w/v of the Kaempferol-loaded $CaCO_3$ MP. The mixture was incubated for 10 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.1% w/v aqueous PRM solution with 0.5M NaCl. This alternating SA and PRM layers were deposited in the identical way until the desired layer number was achieved and finally surface modification by using 0.1% w/v STDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be ~$2\times10^7$ Capsules/ml.

Example-18

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.2% w/v aqueous SA solution containing 0.5M NaCl into 0.5% w/v of the Kaempferol-loaded $CaCO_3$ MP. The mixture was incubated for 20 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.2% w/v aqueous PRM solution with 0.5M NaCl. This alternating SA and PRM layers were deposited in the identical way until the desired layer number was achieved and finally surface modification was carried out using 0.2% w/v STDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be ~$2\times10^7$ Capsules/ml.

Example-19

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.2% w/v aqueous SA solution containing 0.5M NaCl into 1.0% w/v of the Kaempferol-loaded $CaCO_3$ MP. The mixture was incubated for 10 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.2% w/v aqueous PRM solution with 0.5M NaCl. This alternating SA and PRM layers were deposited in the identical way until the desired layer number was achieved and finally surface modification by using 0.2% w/v STDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be ~$2\times10^7$ Capsules/ml.

Example-20

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.2% w/v aqueous SA solution containing 0.5M NaCl into 2.0% w/v of the Kaempferol-loaded $CaCO_3$ MP. The mixture was incubated for 15 minute under gentle shaking. The excess PE's was removed by three repeated refine circles of centrifugation (4000 rpm, 4 min)/washing/re-dispersion in tripled distilled water. Subsequently the PRM layer was deposited using the same procedure with 10 ml 0.2% w/v aqueous PRM solution with 0.5M NaCl. This alternating SA and PRM layers were deposited in the identical way until the desired layer number was achieved and finally surface modification by using 0.2% w/v STDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be ~$2\times10^7$ Capsules/ml.

Example-21

Two bilayer of polyanion (SA) and polycation (PRM) was sequentially adsorbed over the preformed Kaempferol-loaded $CaCO_3$ MP by LbL self-assembly. The first layer was formed by the addition of 10 ml 0.2% w/v aqueous SA solution containing 0.5M NaCl into 3.0% w/v of the Kaempferol-loaded $CaCO_3$ MP. The mixture was incubated for 10 minute under gentle shaking. The excess PE's was removed by three repeated refine circles of centrifugation (4000 rpm, 4 min)/ washing/re-dispersion in tripled distilled water. Subsequently the PRM layer was deposited using the same procedure with 10 ml 0.2% w/v aqueous PRM solution with 0.5M NaCl. This alternating SA and PRM layers were deposited in the identical way until the desired layer number was achieved and finally surface modification by using 0.2% w/v STDC solution containing in 0.5M NaCl by simple adsorption method. These Kaempferol loaded microcapsules were collected by centrifugation, rinsed with tripled distilled water. The concentration of microcapsules was determined by haemocytometer using formula as described in example 6 and was found to be ~$2\times10^7$ Capsules/ml.

D: Characterization of Formulation

Example-22

Infrared (IR) spectra were measured on carefully dried samples embedded in KBr pellets. $CaCO_3$ MP, Kaempferol and Kaempferol-loaded MP were ground to powder before measurement.

Thermo gravimetric analysis curves of the samples $CaCO_3$ MP, Kaempferol, and Kaempferol-loaded MP were collected with a thermo analyzer within a temperature range of 30-900° C. with increasing temperature at the rate of 10° C./min. The degradation temperature of Kaempferol, and $CaCO_3$ MP were found to be 350° C., 550° C. and 650° C. respectively. The $CaCO_3$ MP started to lose weight at 650° C. and lost about 50% weight at 750° C. Free Kaempferol started to lose weight at 350° C. and lost weight about completely at 450° C. The $CaCO_3$-Kaempferol started to lose weight at 550° C., 200° C. higher than that of free Kaempferol. The increase in thermal decomposition temperature of Kaempferol from 350° C. to 550° C. upon encapsulation in $CaCO_3$ MP indicates that some interaction would have occurred between Kaempferol and $CaCO_3$ and there is no drug at the surface of MP.

Powder X-ray patterns were recorded. Typically, the diffract gram of $CaCO_3$ MP, Kaempferol, and Kaempferol-loaded MP were recorded in a 2 θ range of 5-25° C. The diffraction peaks observed in case of Kaempferol is almost absent in XRD of $CaCO_3$-Kaempferol appearing at low 2 θ. Similarly the diffraction pattern of $CaCO_3$ MP has been found to be similar to $CaCO_3$-Kaempferol. This indicates that Kaempferol encapsulated/adsorbed in the nanopore of $CaCO_3$ in amorphous state without crystallization, otherwise the diffraction peaks of Kaempferol would have been observed.

The mean particle size and particle size distribution of $CaCO_3$ MP and fabricated microcapsules by a laser diffraction particle size analyzer. The sample was dispersed in TDW and sonicated at 10% amplitude for 30 second. Optical properties of the sample were defined as follows: refractive index 1.460 and absorption 0.00 (similarly to the particles named Microcapsules in the Malvern software). It reveals that the all the bare MP and fabricated microcapsules were in the range of 3-5 µm and distribution is monodisperse. Each sample was measured in triplicate.

The morphology of the fabricated microcapsules were examined by SEM. Samples were prepared by applying a drop of particle suspension to glass slide and then drying overnight. Then samples were sputtered with gold and measurements were conducted at an operation voltage of 3 KeV. The auto-digestion of core particles from fabricated microcapsules in GI milieu and thus transformation of these microcapsules in to intact nano-walled matrix was shown by the transmission electron microscopy (TEM) as illustrated in FIG. 2B.

Fluorescence photomicrographs were taken. The excitation wavelength was chosen to be 488 nm according to the FITC-labeled substrates. The data were obtained using optical images.

LbL growth was determined by ζ-Potential of each adsorbing layer on the $CaCO_3$-Kaempferol MP dispersed in milli Q water. The ζ-potential value was the average of three successive measurements. LBL growth was confirmed by successful recharging of the particle surface with each deposition cycle. Stepwise polyelectrolyte assembly onto these initially positively charged particles (+21.2 mV) has been monitored by ζ-potential alterations. The ζ-potential of capsules varied between −28.5 mV and +10.9 mV having final coating of SA and PRM respectively and surface was modified with SDC with ζ-potential of −8.9 mV. As oppositely charged species are adsorbed onto the surface of the particles, it is expected that there will be a reversal in the measured ζ-potentials of the particles. Layer depositions result in a continuous growth of the PE film without inducing further aggregation. These observations demonstrate that layer-by-layer technique can be successfully applied to fabricate charged colloidal particles coated with thin polyelectrolyte layers.

E: In Vitro Kaempferol Release

Example-23

For in-vitro release study the ultra sink condition was maintained. Briefly, Dried pure Kaempferol dispersed in PBS, the Kaempferol-loaded $CaCO_3$ MP ($CaCO_3$-Kaempferol) and the encapsulated Kaempferol-loaded microcapsules suspension in same concentration were taken in centrifuge tube in one ml phosphate buffer saline (PBS). Two different pH solutions were used as the release medium [a simulated gastric fluid (SGF) (pH 1.2), prepared by diluting a concentrated HCl solution] and [a simulated intestinal fluid (SIF) (pH 7.4), prepared with 0.02M phosphate buffer saline]. The sample was maintained under horizontal agitation at 37° C. in vortex. At different time intervals the dispersion was centrifuged at 10,000 rpm for 5 min. and the supernatant was assayed for Kaempferol using RP-HPLC method at 370 nm against reagent blank. After each sampling the medium was replaced with fresh buffer. It was also ensured that no extra tiny particles are left in the supernatant. The release was found to be rapid in simulated intestinal fluid (SIF) because the Kaempferol saturation solubility at SIF is, much higher than that in the SGF. The cumulative % Kaempferol release for fabricated microcapsules was found to be 19.2% and 63.5% in SGF and SIF respectively after 24 h.

Example-24

F: Animal Studies (Female Sprague Dawley Rats)

Intestinal Uptake Study of FITC-Labeled Formulated Kaempferol Associated to Polymeric Nanomatrix Kaempferol loaded formulation was fluorescently labeled using fluorescein isothiocynate dextran sulfate (FITC-DEX) to study intestinal uptake in small intestine. The previously FITC tagged formulation suspended in PBS (pH 7.4) and orally administered to overnight fasted adult female Sprague Dawley rats (n=3×2). There was no mortality and all animals survived until they were sacrificed after dosing. Rats were anesthetized with Nembutal 50 mg/kg and euthanized after 1, 3 and 5 h post administration and perfusion was done with chilled PBS followed by 4% paraformaldehyde solution for fixing the tissues. The different intestinal tissue samples were embedded in a cryostat medium, cryofixed in 4% buffered formalin and 5 µm thick frozen sections were prepared using a cryomicrotome. The sections were then viewed using a fluorescence microscope using two separate emission detectors to isolate the dye from background. Intense fluorescence was observed at the tip of the villus and at baso-lateral region of the villus (data not shown).

Figure 4:
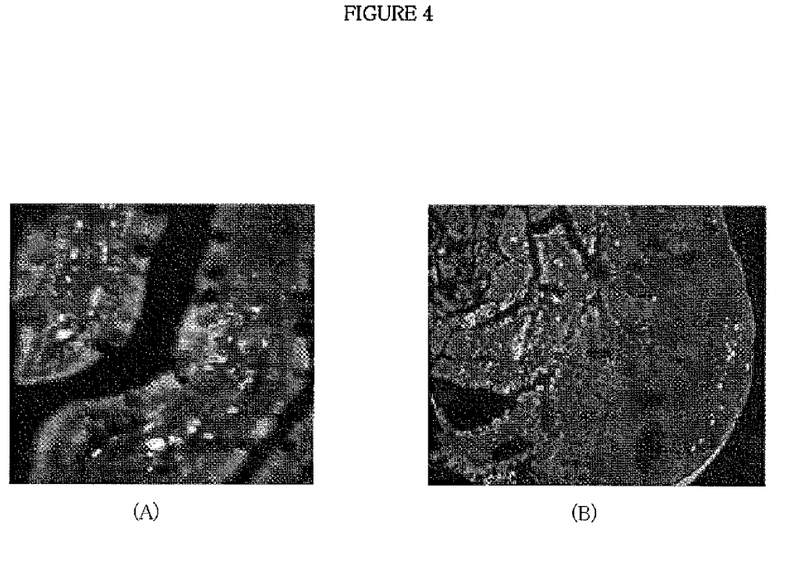
FIG. 4: Fluorescence microscopy of sections slices through intestinal loop (Lymphatic ducts A) (Payer's patches, M cells B) 5 hr after the oral administration of formulation. Photomicrographs A and B were taken at magnification 40× and 10× respectively.

This labeling further continued as isolated fluorescent particles or small clusters mainly in the Peyer's patches which reveals lymphatic uptake via M cells of the Peyer's patches mostly abundant in the ileum as shown in FIG. 4. These results indicate that the formulation is taken up by the intestinal mucosa. The consistent presence of the fluorescent layer over the tip of the villi near the intestinal mucosa indicates that formulation has increased residence time next to absorption surface of the gastrointestinal tract and creates a drug gradient concentration towards blood. This study provides evidences that the formulation has potential for the treatment of osteoporosis.

Example-25

Figure 3:
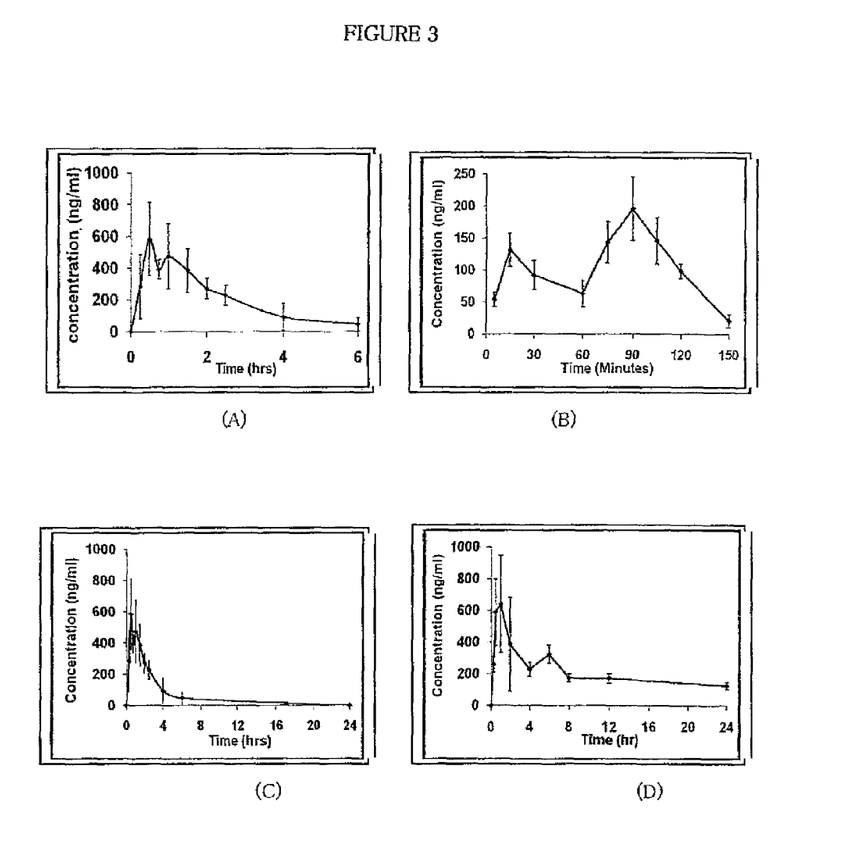
FIG. 3: In vivo PK profile in rat serum and bone marrow following after oral administration of Kaempferol and formulated Kaempferol. The error bars indicates ±S.D of three sets of experiments (n=3). A: Concentration-time profile of Kaempferol in Rat serum; B: Concentration-time profile of Kaempferol in Rat bone marrow; C: Concentration-time profile of Kaempferol-formulation in Rat serum; D: Concentration-time profile of Kaempferol-formulation in Rat bone marrow.

Comparative Bioavailability of Free and Encapsulated Kaempferol in Rat Serum and Bone Marrow Kaempferol (free; 1 mg/kg) in 20% ethanol was orally administered by gavage. Following administration, the rats were sacrificed at 0.25, 0.5, 1.0, 1.5, 2.0, 2.5, 3.0, 4.0, 6.0, and 24 h to obtain serum and bone marrow. After protein precipitation, concentration of Kaempferol in serum and bone marrow was determined by HPLC. Serum pharmacokinetic profile suggests rapid absorption of kaempferol, which appeared to peak (583.44±228.8 ng/ml, $C_{max}$) at 0.5 h ($T_{max}$), with AUC(0-6 h) being 1420.63 ng*h/ml (FIG. 3) and post absorption sharp elimination was noticed, which went below the detection limit after 6 h in serum. In bone marrow $C_{max}$ (194.48 ng/ml) of Kaempferol (free) was found to be at 90 min. of oral administration and the levels went below the detection limit after 2.5 h. Similarly formulated (LbL based assembly) Kaempferol (equivalent to 1 mg/kg of free Kaempferol) was administered orally using gavage. Following administration, the rats were sacrificed at 0.25, 0.5, 1.0, 1.5, 2.0, 2.5, 3.0, 4.0, 6.0, and 24 h to obtain serum and bone marrow. After protein precipitation concentration of Kaempferol in serum and bone marrow was determined by HPLC. The mean serum pharmacokinetics profile (for the three rats at each time point) of kaempferol on administration of formulation was calculated over 24 h. Rapid absorption of Kaempferol is evident, which appeared to peak after 1 h and can be detected for as long as 24 h post administration. The maximum serum concentration (Cmax) of kaempferol at 1 h was 261±148 ng/ml. The area under serum concentration curve (AUC0-24 h) of Kaempferol with formulation was found to be 2479.18 ng*h/ml, which is 1.6 fold higher than free Kaempferol. The Cmax value of kaempferol in bone marrow was found to be 641 ng/ml (60 min.) which is more than three times as compared to free Kaempferol. Therefore, the pharmacokinetic data suggests that with the help of formulation we have been able to prolong the time of action of formulated Kaempferol.

Example-26

Bone Mineral Density (BMD) Measurement in Sprague Dawley Rats after One Month of Oral Administration of Formulation The study was conducted in accordance with current legislation on animal experiments [Institutional Animal Ethical Committee (IAEC)] at C.D.R.I. Forty female Sprague Dawley rats weighing 200 g were taken for the study (n=10/group). Thirty rats were bilaterally ovariectomized (OVx). The other 10 rats were exposed to a sham surgical procedure. All rats were individually housed at 21° C., in 12-h/12-h light-dark cycles. Normal chow diet and water was provided ad libitum. The rats were left for 4 weeks to develop osteopenia. The animals were divided into 4 groups Sham, Ovaticetomized group (Ovx), Ovx+Kaempferol (Ovaticetomized group treated with Kaempferol) and Ovx+F (Ovaticetomized group treated with formulation of Kaempferol). Animals were treated for one month then sacrificed and BMD was determined.

Figure 5:
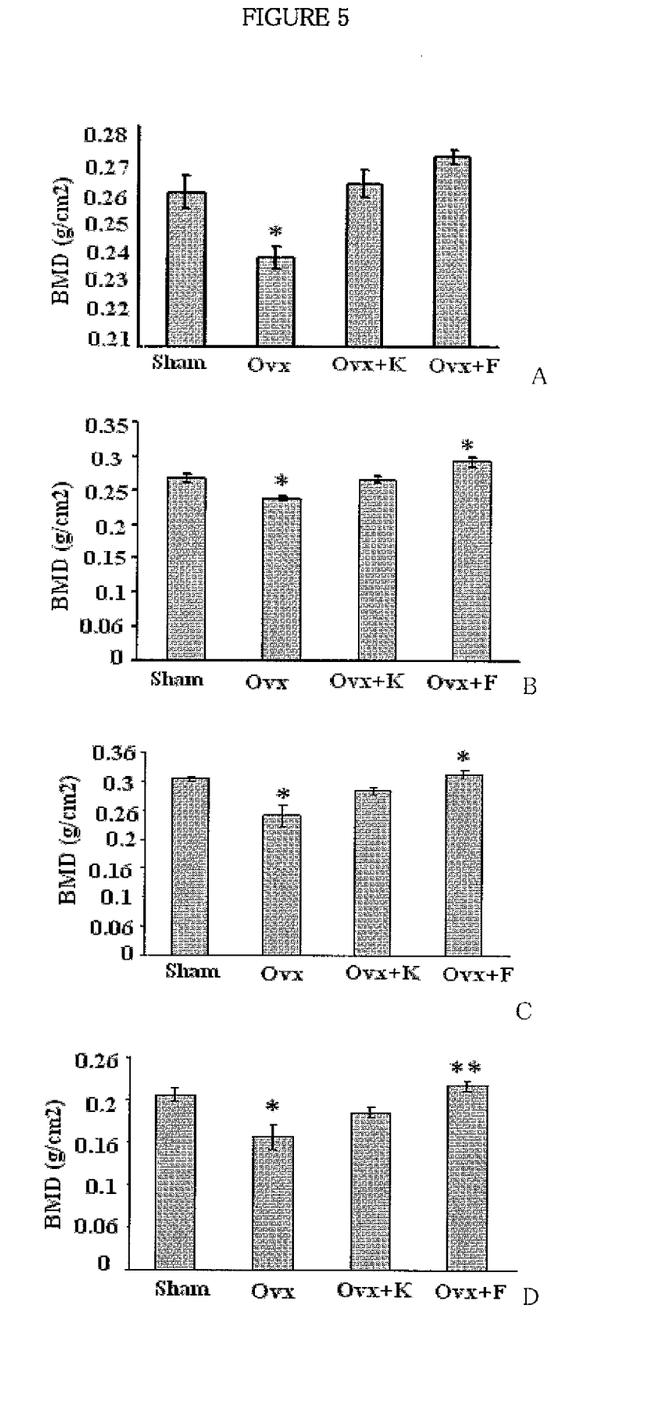
FIG. 5: BMD as measured by DEXA in excised bones (A) Femur global (B) Femur diaphysis (C) Tibia Head (D) Vertebrae global.

BMD was determined by DEXA (Dual Energy X-ray Absorptiometry) using a Hologic QDR 4500A x-ray densitometer with high-resolution small animal software. BMD of the excised bones (left femurs, tibia, and lumbar vertebrae) were studied at the end of experiment. Left femurs were placed on their posterior surfaces, and BMD of the sub-regions was assessed. Distal and proximal regions corresponded to the cancellous bone and central to the cortical bone. Results are given in g/cm$^2$ as represented in FIG. 5. Whereas both OVx+Kaempferol and OVx+F groups exhibited significantly higher trabecular BMD over OVx+vehicle group, it was OVx+F group that afforded significantly better bone mineral density over OVx+Kaempferol group.

TABLE

Bone Mineral Density of (A) Femur global (B) Femur diaphysis (C) Tibia head (D) Vertebrae global after administration of different formulations. (Data are represented as g/cm$^2$). K = Kaempferol; F = Kaempferol loaded formulation.

| Bone Part | Sham | OVx + vehicle | OVx + K | OVx + F |
| --- | --- | --- | --- | --- |
| Femur global | 0.2594 ± 0.012 | 0.23875 ± 0.008 | 0.262 ± 0.01 | 0.2806 ± 0.004 |
| Femur diaphysis | 0.26675 ± 0.16 | 0.23825 ± 0.005 | 0.2658 ± 0.01 | 0.292 ± 0.017 |
| Tibia Head | 0.304 ± 0.007 | 0.2405 ± 0.04 | 0.2835 ± 0.015 | 0.3128 ± 0.018 |
| Vertebrae global | 0.205 ± 0.017 | 0.15625 ± 0.033 | 0.18475 ± 0.013 | 0.216 ± 0.012 |

Bone Strength Measurement, Results are given in g/cm$^2$.

The bone mineral density was found to increase in all excised bones (left femurs, tibia, and lumbar vertebrae) after administration of formulation in OVx animals as compared to vehicle. In case of OVx+F group the bone mineral density was increased by 14%, 20.8%, 22.5% and 37.5% in Femur global, Femur diaphysis, Tibia Head, Vertebrae global respectively as compared to OVx+vehicle group, while the increase was almost 8% in used excised bones as compared to OVx+K group. This indicates that the Kaempferol loaded in layer-by-layer system is able to release the Kaempferol in a controlled fashion and facilitates its uptake in bones.

Example-27

This test predominantly measured trabecular bone strength using a Bone Strength Tester TK-252C (Muromachi Kikai Co. Ltd., Tokyo, Japan). The bone strength for all the groups was measured as reported in this invention.

Figure 6:
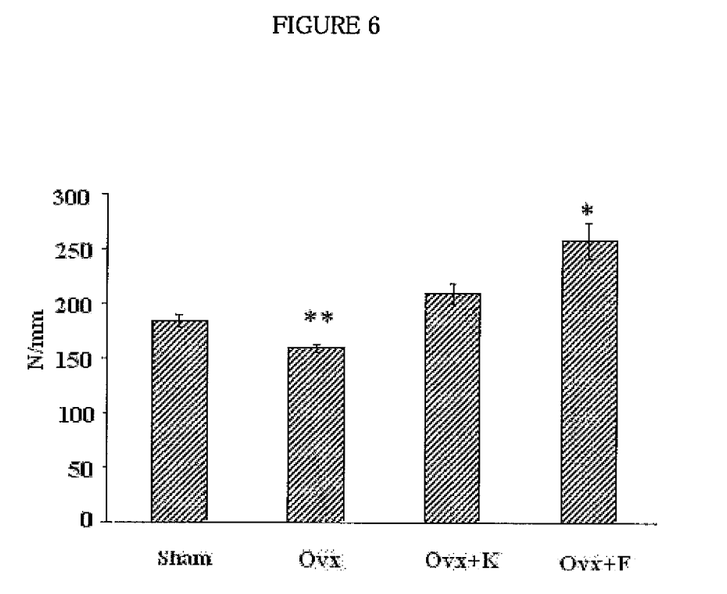
FIG. 6: Bone Strength Measurement on trabecular bone using a Bone Strength Tester TK-252C (Muromachi Kikai Co. Ltd., Tokyo, Japan) after one month treatment of all formulation on female Sprague Dawley rats.

The bone strength data indicates that there is significant loss in bone strength in the ovariectomized group as represented in FIG. 6. This loss is not only recovered after treatment for a month but there is also significant increase in bone strength when Kaempferol bearing formulation was administered. The bone strength was found to increase by 1.6 times approx. with formulation compared to ovariectomized animals as well as sham treated animals. This data shows that with the increase in density of the bone the quality of the bone is also improved.

TABLE

Bone strength in different groups of animals.
(Data has been represented in N/mm)

|  | Sham | OVx + vehicle | OVx + K | OVx + F |
|---|---|---|---|---|
| Bone strength | 184 ± 13.11 | 159 ± 7.25 | 209.4 ± 21.52 | 257.5 ± 38.59 |

K = Kaempferol; F = Kaempferol loaded formulation. (Data are represented as N/mm).

The bone strength data shows that OVx+K and OVx+K groups exhibited significantly higher bone biomechanical strength over OVx+vehicle group, it was OVx+F group that afforded significantly better bone strength over OVx+K group. The bone strength in case of OVx+F was found to increase almost 62% and 23% as compared to OVx+vehicle and OVx+K respectively.

ADVANTAGES OF THE PRESENT INVENTION

The present invention relates to novel, smart, multifunctional biodegradable microcapsules formulation that is in-vivo converted into intact nanomatrix bearing Kaempferol, so that it could overcome all the challenges occurred with the other conventional and novel formulations. As our invention involves the formulations superiority in all the aspects particularly, the present invention also provides: a pharmaceutical composition in accordance with the invention, e.g. as herein described, claimed or exemplified, which is prepared by easy and reproducible LbL adsorption technique. Preferably the compositions in accordance with this aspect of the present invention are generally regarded as safe (GRAS).

At present, little experimental data are available concerning the interaction of PE capsules with biological cells. One important consideration in the passage of capsules through blood vessels is the capsule elasticity. As shown in the atomic-force spectroscopy studies performed by the groups of Fery and Vinogradova, the elasticity of the capsules can be made to vary to within 0.05-10 GPa, depending on the composition, treatment and filling of the capsule. This feature facilitates their use as a delivery system in the circulation. However, no animal data are available using this delivery system. It appears that, instead of their first introduction in 1998 by Decher, et al., capsule technology has not yielded any real applications, particularly data concerning capsule behavior in the bloodstream.

Figure 2:
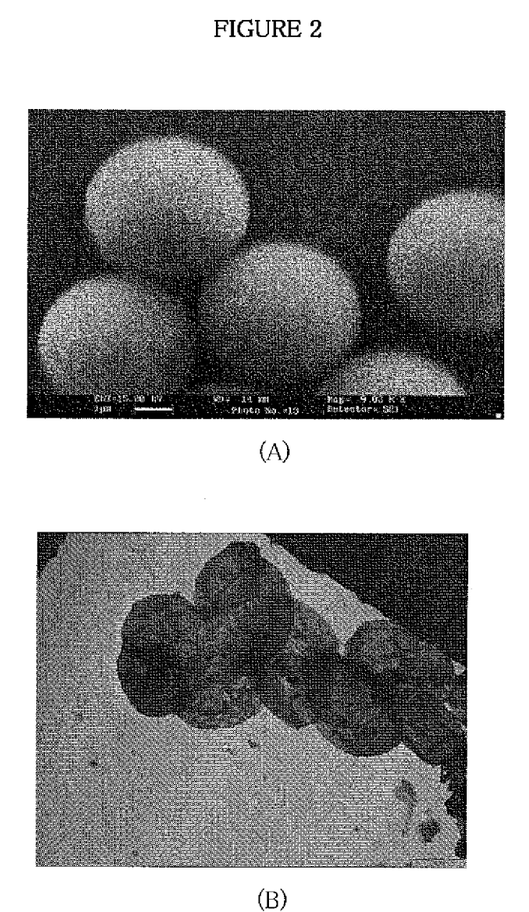
FIG. 2: (A) Scanning Electron Microscopy (SEM) of bare $CaCO_3$ microparticles. Scale bar 1 µm. (B) Transmission Electron Microscopy (TEM) of nanowalled matrix after core removal at gastric pH.

The reports in the literature indicate that there is no commercially available Kaempferol formulation for effective management of osteoporosis. Moreover the bioavailability levels achieved using oral Kaempferol (free) are also low and exhibit wide variation between individuals, individual patient types and even for single individuals at different times during the course of therapy. The novel nanomatirx described herein is based on LbL assembly bearing Kaempferol with bile salt as one of the integral component on the outer surface which has provided improved absorption profile of Kaempferol and improved uptake in bone marrow. This strategy makes our prototype formulation as ideal and safe delivery vehicle for the treatment of osteoporosis. The invention is based on layer-by-layer technology, which involves electrostatic interaction between polyelectrolytes to get a matrix structure which when given orally, the nanomatrix is auto-generated subsequent to dissolution of core particles in gastric fluid (FIG. 2 B) which further control the release of active ingredient and facilitates absorption through small intestine. In an embodiment of the invention wherein the bioavailability of kaempferol in both serum (1.6 fold higher than free Kaempferol) and bone (more than 3 fold higher than free Kaempferol) marrow has been enhanced as compared to free kaempferol. The prior art recites that kaempferol has rapid absorption but at the same time exhibit rapid elimination. To circumvent this problem, the present invention teaches that kaempferol is encapsulated in biodegradable nano-matrix to provide improved uptake in bones by providing Kaempferol release in sustained fashion. This prototype formulation is anticipated to provide enhanced bioavailability of Kaempferol and increased retention in bone marrow thereby enhancing its bone-sparing efficacy under postmenopausal bone loss.

We claim:

1. A microcapsule for controlled release of a flavonoid compound comprising: a core particle consisting of (i) a calcium salt and (ii) a [poly(ethylene oxide-c-polypropylene oxide), block polyoxyethylene-polypropylene block copolymer], loaded with a flavonoid compound, said core particle having a plurality of alternate layers of cationic and anionic polyelectrolytes adsorbed thereon and an outer layer formed by a bile salt, wherein the flavonoid is present in an amount ranging between 10 to 96% by weight of said microcapsule.

2. The microcapsule as claimed in claim 1, wherein the flavonoid compound is selected from the group consisting of quercetin, and its derivatives, kaempferol and its derivatives, rutin, C-glycosylated and O-glycosylated kaempferol.

3. The microcapsule as claimed in claim 1, wherein the polyelectrolyte is selected from a group consisting of naturally occurring polymers including sodium alginate, protamine sulfate chitosan, glycol chitosan and alginate, similarly synthetic polymers including poly allylamine hydrochloride, poly styrene sulfonate, polyornithine bromide, poly ethylene imine and a combinations thereof.

4. The microcapsule as claimed in claim 1, wherein the polyelectrolytes comprises cationic and anionic polyeletrolytes.

5. The microcapsule as claimed in claim 1, wherein the polyelectrolyte is biocompatible and biodegradable.

6. The microcapsule as claimed in claim 1, wherein the polyelectrolyte comprises weak positively charged polyelectrolytes selected from the group consisting of protamine sulfate, chitosan and glycol chitosan, and weak negatively charged polyelectrolytes selected from the group consisting of sodium alginate, dextran sulphate and fluorescein isothiocyanate dextran sulfate.

7. The microcapsule as claimed in claim 1, wherein the naturally occurring polyelectrolyte is selected from the group consisting of sodium alginate, protamine sulfate chitosan, glycol chitosan and alginate.

8. The microcapsule as claimed in claim 1, wherein the core particle is selected from the group consisting of β-tricalcium phosphate, hydroxyapatite, calcium carbonate, calcium sulphate, calcium phosphate, bone and demineralized bone.

9. The microcapsule as claimed in claim 1, wherein the bile salts are selected from the group consisting of sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodiumglyco chenodeoxycholate, sodium cholylsarcosinate and sodium n-methyl taurocholate.

10. The microcapsule as claimed in claim 1, wherein the microcapsule is based on layer-by-layer technology, which involves electrostatic interaction between polyelectrolytes to get a nanomatrix to control the release of active ingredient.

11. A process for preparation of microcapsule for controlled release of flavonoid as claimed in claim 1, wherein the process steps comprising;

(a) mixing equimolar concentration of calcium chloride dehydrate and sodium carbonate in presence of [poly(ethylene oxide co-polypropylene oxide) block polyoxyethylene polypropylene block copolymer] to obtain porous, spherical and homogeneously dispersed particles of $CaCO_3$ micro particles, (b) incubating $CaCO_3$ micro particles with flavonoid in monohydric alcohol as a solvent for a period ranging between 12 to 36 h and finally washing thoroughly and drying under vacuum at a temperature ranging between 30 to 50 degree C., (c) depositing alternatively, the oppositely charged weak polyelectrolytes on flavonoid loaded $CaCO_3$-kaempferol using layer-by-layer assembly to obtain polyeletrolyte nanomatrix, (d) incubating said polyeletrolyte nanomatrix with a solution of bile salt for surface modification at a temperature ranging between 20 to 40 degree centigrade for a period ranging between 30 minutes to two hr, centrifuging followed by washing with water to obtain the microcapsule.

12. A method for enhancing levels of flavonoid in serum and bone marrow of a subject comprising orally administering the microcapsule of claim 1 to said subject.

13. A method for inducing an osteogenic effect in bone tissue of a mammalian subject comprising administering an amount of the microcapsule of claim 1 to said mammalian subject in combination with a pharmaceutically acceptable excipient, to induce said osteogenic effect.

\* \* \* \* \*